(12) United States Patent
Meglin

(10) Patent No.: US 6,524,300 B2
(45) Date of Patent: Feb. 25, 2003

(54) INFUSION CATHETER WITH NON-UNIFORM DRUG DELIVERY DENSITY

(75) Inventor: Allen J. Meglin, Wilmington, NC (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 09/738,759

(22) Filed: Dec. 15, 2000

(65) Prior Publication Data

US 2001/0053896 A1 Dec. 20, 2001

Related U.S. Application Data
(60) Provisional application No. 60/177,874, filed on Jan. 24, 2000, and provisional application No. 60/174,472, filed on Jan. 3, 2000.

(51) Int. Cl.[7] .............................................. A61H 25/00
(52) U.S. Cl. ............................ 604/523; 604/9; 604/30; 604/246; 604/264; 604/537
(58) Field of Search .................. 604/246, 264, 604/500, 523, 525, 528, 537, 9, 30, 43, 167.04, 247

(56) References Cited

U.S. PATENT DOCUMENTS

| | | | |
|---|---|---|---|
| 3,888,249 A | 6/1975 | Spencer | 128/214 R |
| 4,973,319 A | 11/1990 | Melsky | 604/247 |
| 5,250,034 A | 10/1993 | Appling et al. | 604/164 |
| 5,267,979 A | 12/1993 | Appling et al. | 604/247 |
| 5,817,072 A * | 10/1998 | Lampropoulos et al. | 604/264 |
| 5,957,901 A * | 9/1999 | Mottola et al. | 604/264 |
| 6,063,069 A * | 3/2000 | Cragg et al. | 604/508 |
| 6,107,004 A * | 8/2000 | Donadio, III | 430/320 |
| 6,109,269 A * | 8/2000 | Rise et al. | 128/898 |
| 6,179,816 B1 * | 1/2001 | Mottola et al. | 604/264 |
| 6,306,124 B1 * | 10/2001 | Jones et al. | 604/509 |

OTHER PUBLICATIONS

"Instructions for use. Fountain™ Infusion System." Merit Medical Systems, Inc. South Jordan, Utah. 7 pgs. (In use before Jan. 3, 2000).
"Cragg–McNamara™ Valved Infusion Catheter." Micro Therapeutics, Inc., Irvine, California, 1 page (In use before Jan. 3, 2000).

* cited by examiner

Primary Examiner—Charles G. Freay
Assistant Examiner—John F Belena
(74) Attorney, Agent, or Firm—Wolf, Greenfield & Sacks, P.C.

(57) ABSTRACT

An infusion catheter has a plurality of exits whose distribution of sizes or positions produces a variation in delivery rate and pressure of a drug or other medical preparation over an infusion region. The exits may be holes or slits. A method of infusing a medical agent, infuses the agent at a rate which is non-uniform over a length of infusion.

15 Claims, 1 Drawing Sheet

INFUSION CATHETER WITH NON-UNIFORM DRUG DELIVERY DENSITY

CROSS-REFERENCE TO RELATED APPLICATIONS

This application claims domestic priority under 35 U.S.C. §119(e) to provisional U.S. Patent Applications Ser. No. 60/174,472, filed Jan. 3, 2000, and Ser. No. 60/177,874, filed Jan. 24, 2000, and incorporated herein in their entirety by reference.

FIELD OF THE INVENTION

The present invention relates generally to devices for delivering a drug or other medical preparation to a site within a patient's body. More particularly, the invention relates to catheters, which deliver drugs or other medical preparations to a site within a lumen of a blood vessel or another cavity within a patient's body.

BACKGROUND OF THE INVENTION

Catheters for delivering to a site within a patient's body a drug or other medical preparation are known. Two such catheters are the Fountain™ Infusion System (Merit Medical Systems, Inc., Utah) and the Cragg-McNamara™ Valved Infusion Catheter (Micro Therapeutics, Inc., California).

One example of the Fountain device is now described. This particular example, catalog number FIS5-135-5 is a 135 cm long tube having a 5 cm infusion segment. The infusion segment is located at a distal end of the device, intended to be inserted into a blood vessel of a patient through a tiny incision or puncture. The Fountain catheter of this example is 5 French (1.7 mm) outside diameter, and accepts through a lumen a 0.035 inch (0.80 mm) diameter guide wire for placement. The infusion segment of the Fountain device includes, distributed uniformly along the length of the infusion segment, a plurality of holes at a density of 10 minute holes each 2 cm, through which a drug or other medical preparation introduced into the lumen, can be infused into the vessel in which the catheter is inserted. The catheter further includes two radiopaque markers at the boundaries of the infusion segment, whereby the catheter is guided using fluoroscopy to the desired site.

An example of the Cragg-McNamara device is now described. Micro Therapeutics, Inc. catalog number 41046-01 is similar to the Fountain device described above. The device is a 5 French (1.7 mm) diameter catheter, 65 cm long, with a 5 cm infusion segment. The lumen of the catheter is large enough to accept a 0.035 inch (0.80 mm) diameter guide wire, and the infusion segment is marked at the boundaries thereof by radiopaque markers. The infusion segment of this conventional device includes, distributed uniformly along the length of the infusion segment, a plurality of holes at a density of 4 minute holes each 2 cm, through which a drug or other medical preparation introduced into the lumen can be infused into the vessel in which the catheter is inserted.

Two catheters with pressure responsive valves, such as slits, forming exits through the wall thereof are disclosed by Appling et al. in U.S. Pat. Nos. 5,250,034 and 5,267,979, both incorporated herein by reference. The catheters of those patents feature a uniform distribution of such exits.

SUMMARY OF THE INVENTION

In accordance with the principles of the present invention, there may be provided an infusion catheter having an infusion segment defined to produce a non-uniform distribution of infusion of drug or other medical preparation. The non-uniform distribution of infusion may be produced by a non-uniform pattern of exits, such as holes or slits, defined in the infusion segment. The non-uniform pattern of exits may include plural regions of different uniform distributions of exits. The non-uniform pattern of exits may include plural regions of exits of different sizes, such as slits of different lengths.

According to one aspect of the invention, an infusion catheter comprises: an elongated catheter body defining a catheter lumen, the catheter body having a proximal end at which a medical agent can be introduced into the catheter lumen, and having an infusion segment defined at a distal end; the infusion segment including a non-uniform pattern of infusion exits through the catheter body to the catheter lumen. According to one variation of the infusion catheter, the non-uniform pattern of exits comprises a first region with an exit density of about 1–10 infusion exits per 2 cm of length; and a second region with an exit density of about 25–30 infusion exits per 2 cm of length. In this variation, at least one of the first and second regions can have a substantially uniform exit distribution. Also according to this variation, the second region can be located more distal relative to the first region. Alternatively, according to this variation, the first region can be located more distal relative to the second region. The pattern of exits can vary continuously from the first region to the second region. At least one infusion exit can be smaller than a 30 gauge needle. At least one infusion exit can be a slit. In another variation of this aspect of the invention, the non-uniform pattern of infusion exits can include plural infusion exits of varying sizes. The plural infusion exits of varying sizes can be slits of varying lengths. The non-uniform pattern of infusion exits can include a first region of slits of a first length; and a second region of slits of a second length. The lengths of the slits can be arranged to vary continuously from the first length to the second length between the first region and the second region. At least one of the first and second regions can have a substantially constant slit length throughout.

According to another aspect of the invention, a method of infusing a medical agent into a target lumen of a body, comprises inserting a catheter into the target lumen, injecting the medical agent into a lumen of the catheter, and ejecting the medical agent from the lumen of the catheter into the target lumen of the body at a rate which is not uniform over an infusion segment of the catheter.

BRIEF DESCRIPTION OF THE DRAWING

In the drawing in which like reference designations indicate like elements.

DETAILED DESCRIPTION OF EMBODIMENTS OF THE INVENTION

The present invention may be embodied in a catheter of any convenient length. At a distal end thereof, the catheter includes an infusion segment having a non-uniform distribution of holes along the length thereof.

A range of catheter sizes is useful in particular applications. Many applications are served by a 5 French (1.7 mm)

diameter catheter. A 4 French catheter is useful in somewhat smaller vessels than would be a 5 French device. A 3 French or 2 French catheter is useful in the much smaller intracerebral vessels, for example. However, the invention is not limited to any particular one or group of these discrete sizes.

Catheters embodying the present invention are useful for infusing various medical preparations including therapeutic agents and diagnostic agents for therapeutic or diagnostic purposes.

Figure 1:
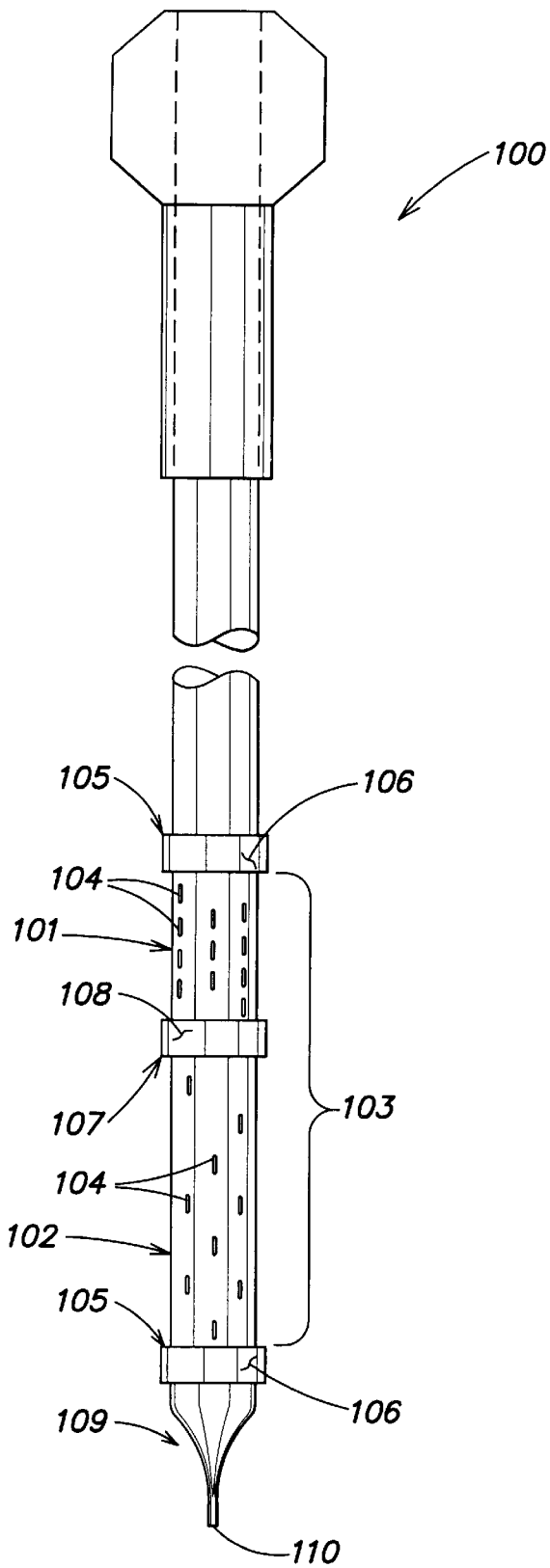
FIG. 1 is a side schematic view of one embodiment of the invention.

One embodiment of the invention, described herein in connection with FIG. 1, is useful in connection with maintaining a femoral artery bypass graft in a clot-free state. It is well-known that such grafts tend to occlude over time, due to the formation of a blood clot on the inner surface of the lumen of the graft. Previously urokinase (UK) was introduced at the clot site using a conventional infusion catheter, such as one of those described above, to lyse, i.e., dissolve, the clot. More recently, clots in such grafts have been lysed using tissue plasminogen activator (TPA), similarly introduced using a conventional infusion catheter. However, it has now been observed that differential lysis of the clot occurs within the graft when using TPA. That is, the more distal portions of the clot (near the outflow end of the graft) lyse more quickly than the more proximal portions of the clot (near the inflow end of the graft). It has further been observed by this inventor that in an effective therapy using UK, UK is infused at a total flow rate of about 50–100 cc/hour, whereas in an effective therapy using TPA, TPA is infused at a total flow rate of about 2–4 cc/hour at the outflow end of the graft and about 12–25 cc/hour at the inflow end of the graft. Studies of clots removed from such grafts show that the inflow end of the graft has 5–6 times the number of layers of fibrin in the clot compared to the outflow end of the graft. This inventor has concluded that the greater flow rate used with UK effectively assisted in the process of breaking up and dissolving the clot to such a degree that any differential in effect at one end of the clot compared to the other was rendered negligible.

In order to render TPA, the presently preferred therapeutic agent, more uniformly effective in this application, the embodiment of the present invention shown in FIG. 1 provides two distinct regions 101, 102 within the infusion segment 103 of an infusion catheter 100. One region 102, located for example at the distal end of the catheter 100, includes a pattern of between 1 and 10 holes 104 each cm of length, for example about 5 holes 104 each 2 cm of length, while a second region 101 adjacent the first region 102, and located for example toward the proximal end of the catheter 100 relative to the first region 102, includes a pattern of 10–50 holes 104 each 2 cm of length, for example about 25 holes 104 each 2 cm of length. In the pattern described above, holes 104 can also be slits, for example as shown and discussed below in connection with FIG. 3. Also, the lengths of the regions can be greater or less than the example, above.

The boundaries 105 of the infusion segment 103 are preferably marked by radiopaque marker bands 106, for example molded into the catheter tube or crimped onto the catheter 100. Moreover, the boundary 107 between the two regions 101, 102 within the infusion segment 103 is also preferably marked by a radiopaque marker band 108. Thus, the precise positioning of the infusion segment 103 relative to the inflow and outflow ends of the clot can be achieved by fluoroscopy. Alternatively, ultrasonically contrasting markers 106, 108 can mark the regions of the infusion segment 103 for placement using ultrasonic visualization.

Depending on whether the catheter is intended for insertion in the direction of blood flow or against the direction of blood flow, the higher density of infusion holes could be located toward either the distal or proximal end of the catheter relative to the location of the lower density of infusion holes. The principle behind selecting the correct orientation for the infusion hole density is that the higher density of holes should align with the thicker portion of the clot to be treated (usually the inflow end), while the lower density of holes should align with the thinner portion of the clot to be treated (usually the outflow end).

Figure 2:
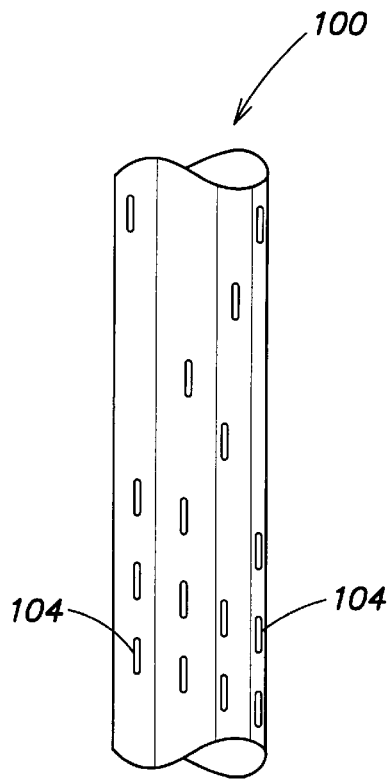
FIG. 2 is a side view of a detail of an infusion segment with a continuously variable hole density.

The infusion segment holes 104 can be laser cut or can be formed by any other known process, such as needle punching, or others. If slits are used, as mentioned above and described below in connection with FIG. 3, they may be formed using fine knives or lasers to cut the catheter without removing material. Conveniently, the patterns of holes can define multiple helixes about the periphery of the catheter tube, or other patterns convenient for manufacture or to provide a desired drug infusion pattern can be used. The infusion segment need not be divided into discrete regions with different hole densities, but rather the hole density may vary in a continuous fashion from one end of the infusion segment to the other, as shown in FIG. 2.

All the laser cut holes can be the same, preferably small, size. Infusion rate is controlled by the density of holes in a location of the infusion segment, with greater hole density providing greater drug infusion rates. Because laser cut infusion holes are typically smaller than 30 gauge needles, the drug is infused into the clot as numerous microjets, which tends to more effectively penetrate the clot material. In order to enhance the microjet action, preferably the holes are as small as possible, causing the therapeutic agent to spray from the holes at very high velocity, but with a low overall flow rate. In a variant relying on this spray action, the holes can be short slits, such as used in the catheters disclosed in U.S. Pat. Nos. 5,250,034 and 5,267,979, as mentioned above.

Figure 3:
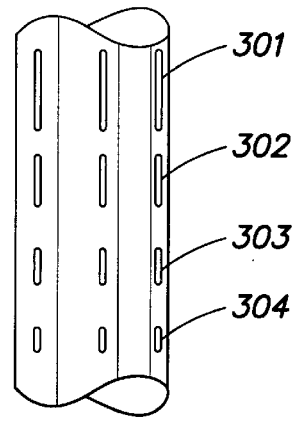
FIG. 3 is a side view of a detail of an infusion segment with slits of varying lengths.

In embodiments of the invention employing slits, an infusion rate, which varies from one position within the infusion segment to another, can be achieved various ways. For example, slit density can be varied as described and illustrated above in connection with holes (See FIGS. 1 and 2). Alternatively, slit lengths can be varied from one region in the infusion segment to another region in the infusion segment, or continuously as shown in FIG. 3. In FIG. 3, slits 301 are longer than slits 302, which are longer than slits 303, which are longer than slits 304.

Several patterns of hole (or slit) density or slit length are possible.

Referring back to FIG. 1, a catheter according to the principles of the invention embodying any of the features described above can have a tapered end 109, with an orifice 110 defined therein. Preferably, the orifice 110 is of a size that can be fully or nearly fully occluded by a guide wire (not shown) or an occluding ball wire (also not shown), for example 0.035 inches (0.80 mm) in inside diameter for a 0.035 inch (0.80 mm) diameter guide wire or occluding ball wire. Such an orifice 110 can infuse the lysing agent discussed above below the region of the clot, so that debris and pieces of clot which may break off due to action of the lysing agent on the clot can be broken up as they travel downstream of the graft, thus avoiding having them form the core of a further thrombus or embolus. Use of an occluding ball wire improves the control of the pressure and flow of lysing agent at different locations.

Use of a guide wire or occluding ball wire in a size admitting such a wire, for example a 4 french or 5 french catheter, is optional.

What is claimed is:

1. An infusion catheter comprising:

an elongated catheter body defining a catheter lumen, the catheter body having a proximal end at which a medical agent can be introduced into the catheter lumen, and having an infusion segment defined at a distal end;

the infusion segment including a non-uniform pattern of infusion exits constructed to disperse a variable density of medical agent through the catheter body to the catheter lumen.

2. The infusion catheter of claim 1, wherein the non-uniform pattern of exits comprises:

a first region with an exit density of about 1–10 infusion exits per 2 cm of length; and a second region with an exit density of about 25–30 infusion exits per 2 cm of length.

3. The infusion catheter of claim 2, wherein at least one of the first and second regions has a substantially uniform exit distribution.

4. The infusion catheter of claim 2, wherein the second region is located more distal relative to the first region.

5. The infusion catheter of claim 2, wherein the first region is located more distal relative to the second region.

6. The infusion catheter of claim 2, wherein the pattern of exits varies continuously from the first region to the second region.

7. The infusion catheter of claim 2, wherein at least one infusion exit is smaller than a 30 gauge needle.

8. The infusion catheter of claim 2, wherein at least one infusion exit is a slit.

9. The infusion catheter of claim 1, wherein the non-uniform pattern of infusion exits comprises:

plural infusion exits of varying sizes.

10. The infusion catheter of claim 9, wherein the plural infusion exits of varying sizes are slits of varying lengths.

11. The infusion catheter of claim 10, wherein the non-uniform pattern of infusion exits comprises:

a first region of slits of a first length; and a second region of slits of a second length.

12. The infusion catheter of claim 11, wherein lengths of the slits vary continuously from the first length to the second length between the first region and the second region.

13. The infusion catheter of claim 11, wherein at least one of the first and second regions has a substantially constant slit length throughout.

14. A method of infusing a medical agent into a target lumen of a body, comprising: inserting a catheter into the target lumen; injecting the medical agent into a lumen of the catheter; and ejecting the medical agent from the lumen of the catheter into the target lumen of the body at a rate which is not uniform and with variable density over an infusion segment of the catheter.

15. An infusion catheter comprising: an elongated catheter body defining a catheter lumen, the catheter body having a proximal end at which a medical agent can be introduced into the catheter lumen, and having an infusion segment defined at a distal end; the infusion segment including a pattern of infusion exits through the catheter body to the catheter lumen, wherein the pattern is arranged such that a substantially higher density of infusion exits is located toward one of the distal end and the proximal end relative to the location of a substantially lower density of infusion exits, in order to produce a non-uniform flow rate with variable density from the infusion exits along the catheter body.

* * * * *